United States Patent [19]
Haimovich et al.

[11] Patent Number: 5,540,736
[45] Date of Patent: Jul. 30, 1996

[54] TRANSCRANIAL ELECTROSTIMULATION APPARATUS HAVING TWO ELECTRODE PAIRS AND INDEPENDENT CURRENT GENERATORS

[76] Inventors: Yechiel Haimovich, 15 Hatayasim, 70400 Nes Ziona; Serge Pyatigorsky, 304/35 Margalit, Gilo, Jerusalem; Felix-Azriel Kochubievsky, 4/1 Moshe Mizrachi, Rehovot, all of Israel

[21] Appl. No.: 360,545

[22] Filed: Dec. 21, 1994

Related U.S. Application Data

[63] Continuation-in-part of Ser. No. 100,855, Aug. 2, 1993, abandoned.

[51] Int. Cl.$^6$ .................................................. A61N 1/36
[52] U.S. Cl. .......................................... 601/46; 607/47
[58] Field of Search ............................... 607/45–47

[56] References Cited

U.S. PATENT DOCUMENTS

| | | |
|---|---|---|
| 4,140,133 | 2/1979 | Kastrubin et al. |
| 4,305,402 | 12/1981 | Katims . |
| 4,327,322 | 4/1982 | Yukl ............................. 607/46 |
| 4,541,432 | 9/1985 | Molina-Negro et al. ........ 607/46 |
| 4,646,744 | 3/1987 | Capel ........................... 607/46 |
| 4,709,700 | 12/1987 | Hyrman . |
| 4,754,759 | 7/1988 | Allocca ......................... 607/46 |
| 4,844,075 | 7/1989 | Liss et al. ...................... 607/45 |
| 5,269,302 | 12/1993 | Swartz et al. . |
| 5,342,410 | 8/1994 | Braverman .................... 607/45 |

OTHER PUBLICATIONS

Joy, M. L. G. et al, "Low Frequency Current Density Imaging in Rabbits", Annual Fall Meeting of the Biomedical Engineering Society (1993).
Joy, M. et al "In Vivi Detection of Applied Electric Currents by Magnetic Resonance Imaging", Magnetic Resonance Imaging, vol 7 pp. 89–94 (1989).
Krupitsky, E. M. et al, "The Administration of Transcranial Electric Treatment for Affective Disturbances Therapy in Alcoholic Patients", Drug and Alcohol Dependence 27 (1991) 1–6.
Rees, H. et al, "The Anterior Pretectal Nucleus: A Proposed Role in Sensory Processing", Pain, 53 (1993) 121–135.
Jones, B. "83C51FA/FB PCA Cookbook", Intel Application Note AP–415.
Smith et al, "Electronarcosis By A Combination of Direct and Alternating Current", *The American Journal of Medical Electronics*, Jan.–Mar. 1965, pp. 38–41.

*Primary Examiner*—William E. Kamm
*Assistant Examiner*—Carl H. Layno
*Attorney, Agent, or Firm*—Mark M. Friedman

[57] ABSTRACT

Transcranial electrostimulation apparatus including two current generators for providing electrical currents, two electrode pairs for detachable attachment to the scalp of a patient of which each is driven by an electrode pair dedicated current generator and control apparatus for independently controlling each current generator such that each electrode pair administers an independently regulated electrical current.

12 Claims, 5 Drawing Sheets

TRANSCRANIAL ELECTROSTIMULATION APPARATUS HAVING TWO ELECTRODE PAIRS AND INDEPENDENT CURRENT GENERATORS

The present application is a Continuation-in-Part of U.S. Pat. application Ser. No. 08/100,855 filed Aug. 2, 1993 now abandoned.

FIELD AND BACKGROUND OF THE INVENTION

The present invention relates to bio-electric apparatus for cranial electrotherapy stimulation in general and in particular to transcranial electrostimulation (TCES) apparatus for inducing analgesia and similar effects.

It has been demonstrated that non-invasive bio-electric stimulation of certain portions of the brain can achieve analgesic effects. In particular, it has been demonstrated that analgesia can be best effected by stimulation of homeostatic endorphinergic mechanism of the brain structure as described in an article entitled "The anterior pretectal nucleus", by H. Rees and M. H. T. Roberts, Pain Volume 53, No. 2, May 2, 1993. Up to the present time, transcranial electrostimulation has been used to treat acute and chronic pain, such as low back pain, headaches, trigeminal neuralgia, post-herpetic neuralgia, and other disturbed body syndromes.

Reference is also made to an article entitled "Low Frequency Current Density Imaging in Rabbits" by M. L. G. Joy, 1993 Annual Fall Meeting of the Biomedical Engineering Society, Memphis State University, Memphis, Tenn., Oct. 21–24, 1993. Still further, reference is made to an article entitled "The administration of transcranial electric treatment for affective disturbances therapy in alcoholic patients" by E. M. Krupitsky, Drug and Alcohol Dependence, 27 (1991) 1–6, Elsevier Scientific Publishers Ireland Ltd.

It is well known that bio-electric stimulation apparatus is best implemented using current sources rather than voltage sources because treatment regimes are determined in terms of the current required to achieve a particular therapeutic effect. Current sources accommodate for changes in impedance caused, for example, by movements of electrodes on the scalp of a patient, the drying out of gel used as the electrical conducting medium between electrodes and the scalp of a patient, and the like without operator intervention.

The shortest, and therefore the most effective, transcranial path traversing the desired mid-brain portion is between the rear of the scalp of a patient and his forehead as described U.S. Pat. No. 4,140,133 to Kastrubin entitled "Device for Pulse Current Action on Central Nervous System". However, deployment of electrodes across such a transcranial path would require shaving the rear portion of the patient's scalp. Since most patients prefer not to have a portion of their scalp shaved, typically two electrode pairs are employed. Typically, one electrode pair is deployed across a transcranial path extending between a patient's left mastoid area and his forehead and the other electrode pair is deployed across a transcranial path extending between a patient's right mastoid area and his forehead. In this case, the first electrode pair stimulates the left side of the patient's mid-brain and the second electrode pair stimulates the right side of the patient's mid-brain.

Thus, as shown in FIG. 1a, conventional TCES apparatus includes a current source based signal generator providing an electrical signal in the form of square shaped pulses to two electrode pairs detachably attached to a patient's scalp as described above. Furthermore, TCES apparatus includes a control unit having a user interface for setting the average current amplitude of the pulses. The electrical pulses are administered at a frequency of about 77 Hz.

The major disadvantage of conventional TCES apparatus is due to the signal generator being connected in parallel to two electrode pairs. This means that a physician has no control over the individual electrode currents due to different impedances caused by physiological and anatomical differences between the left and right sides of a patient's midbrain portion, the quality of the conducting medium, and the like. Thus, as can be clearly seen in FIG. 1b, in the present case, the current traversing the right electrode pair is greater than the current traversing the left electrode pair.

The parallel connection also means that there is no control over the division of a pulse traversing the left transcranial path and the right transcranial path. Hence, even through the signal generator provides a square pulse, the fractions of the pulse delivered by the right and left electrode pairs have an indeterminate shape as shown in FIGS. 1b and 1c.

All in all, the design of conventional TCES apparatus often leads a physician to set the current amplitude to too high a setting than is necessary to achieve the desired therapeutic effect. In contradiction to the motivation behind TCES apparatus, it is well known that many patients even complain of burning sensations during treatment sessions!

There is therefore a need for transcranial electrostimulation apparatus (TCES) which overcomes the above-mentioned disadvantages of conventional TCES apparatus.

SUMMARY OF THE INVENTION

The present invention is for transcranial electrostimulation apparatus.

Hence, there is provided according to the teachings of the present invention, transcranial electrostimulation apparatus comprising: (a) at least two current generators for providing electrical currents, the electrical currents including pulses; (b) at least two electrode pairs for detachable attachment to the scalp of a patient, each of the at least two electrode pairs being driven by an electrode pair dedicated current generator; and (c) controller unit for independently controlling each of the at least two current generators such that each of the at least two electrode pairs administers an independently regulated electrical current.

According to a further feature of the present invention, wherein the control means regulates the current amplitude of the pulses.

According to a still further feature of the present invention, wherein the control means regulates the duration of the pulses.

According to a yet still further feature of the present invention, wherein the control means regulates the frequency of the pulses.

According to a yet still further feature of the present invention, wherein the pulses are substantially square shaped.

According to a yet still further feature of the present invention, wherein the pulses are superimposed on a smooth current.

According to a yet still further feature of the present invention, wherein the electrical current is a zero net charge current in which the product of a negative smooth current amplitude by the time duration between consecutive pulses equals the product of a positive pulse current amplitude by the pulse time duration.

According to a yet still further feature of the present invention, wherein the electrical current is a time-variant electrical stimulatory current which tends to sweep across the homeostatic endorphinergic mid-brain structures of a patient.

According to a yet still further feature of the present invention, wherein each of the at least two current generators includes a bilateral current source.

According to a yet still further feature of the present invention, the apparatus further comprising: (d) a rechargeable battery for driving the at least two current generators; and (e) a port for receiving either a connector connected to an external power supply so as to charge the rechargeable battery or a connector for connecting the at least two electrode pairs to the at least two current generators.

According to a yet still further feature of the present invention, the port includes at least three pins wherein two of the at least three pins are employed for connecting the rechargeable battery to the external power supply.

According to a yet still further feature of the present invention, the port includes at least three pins wherein two of the at least three pins are employed for connecting the at least two current generators to the at least two electrode pairs.

There is also provided according to the teachings of the present invention, apparatus comprising: (a) a rechargeable battery; (b) processing means driven by the rechargeable battery; and (c) a port for receiving either a connector connected to an external power supply so as to charge the rechargeable battery or a connector for connecting the processing means with an output device.

According to a further feature of the present invention, the port includes at least three pins wherein two of the at least three pins are employed for connecting the rechargeable battery to the external power supply.

According to a further feature of the present invention, the port includes at least three pins wherein two of the at least three pins are employed for connecting the processing means to the output device.

BRIEF DESCRIPTION OF THE DRAWINGS

These and further construction features of the invention will be better appreciated in the light of the ensuing description of a preferred embodiment thereof, given by way of example only with reference to the accompanying drawings, wherein.

DETAILED DESCRIPTION OF THE PREFERRED EMBODIMENT

The present invention is of transcranial electrostimulation apparatus.

The principles and operation of the transcranial electrostimulation apparatus according to the present invention may be better understood with reference to the drawings and the accompanying description.

Figure 1A:
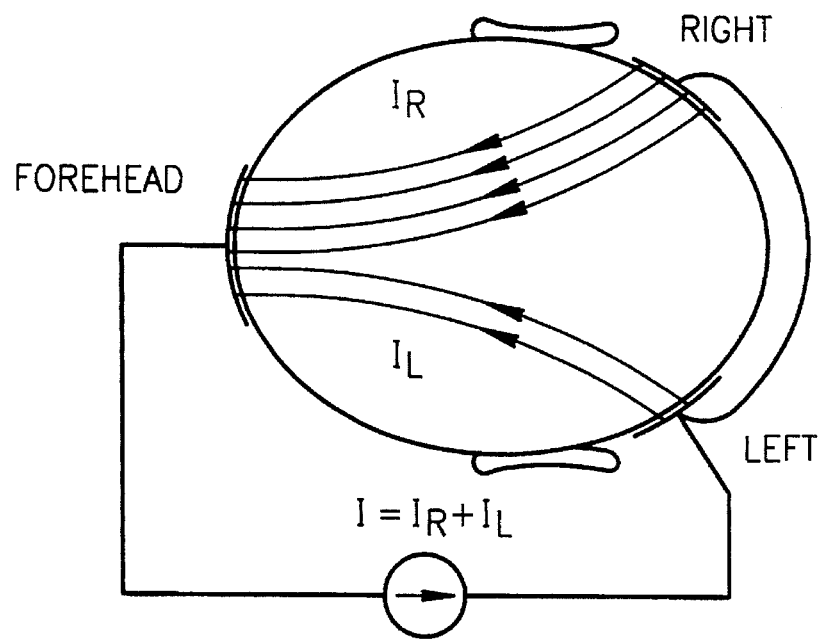
FIG. 1a illustrates a conventional TCES apparatus including a single current generator for administering an electrical current to two electrode pairs connected in parallel.
Figure 1B:
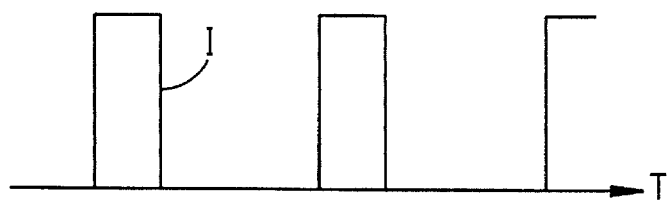
FIG. 1b illustrates a square shape pulse administered by the current generator of the conventional TCES apparatus.
Figure 1C:
FIG. 1c illustrates the pulse administered by the left electrode pair.
Figure 1D:
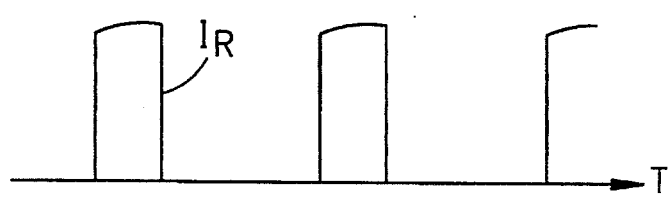
FIG. 1d illustrates the pulse administered by the right electrode pair.
Figure 2:
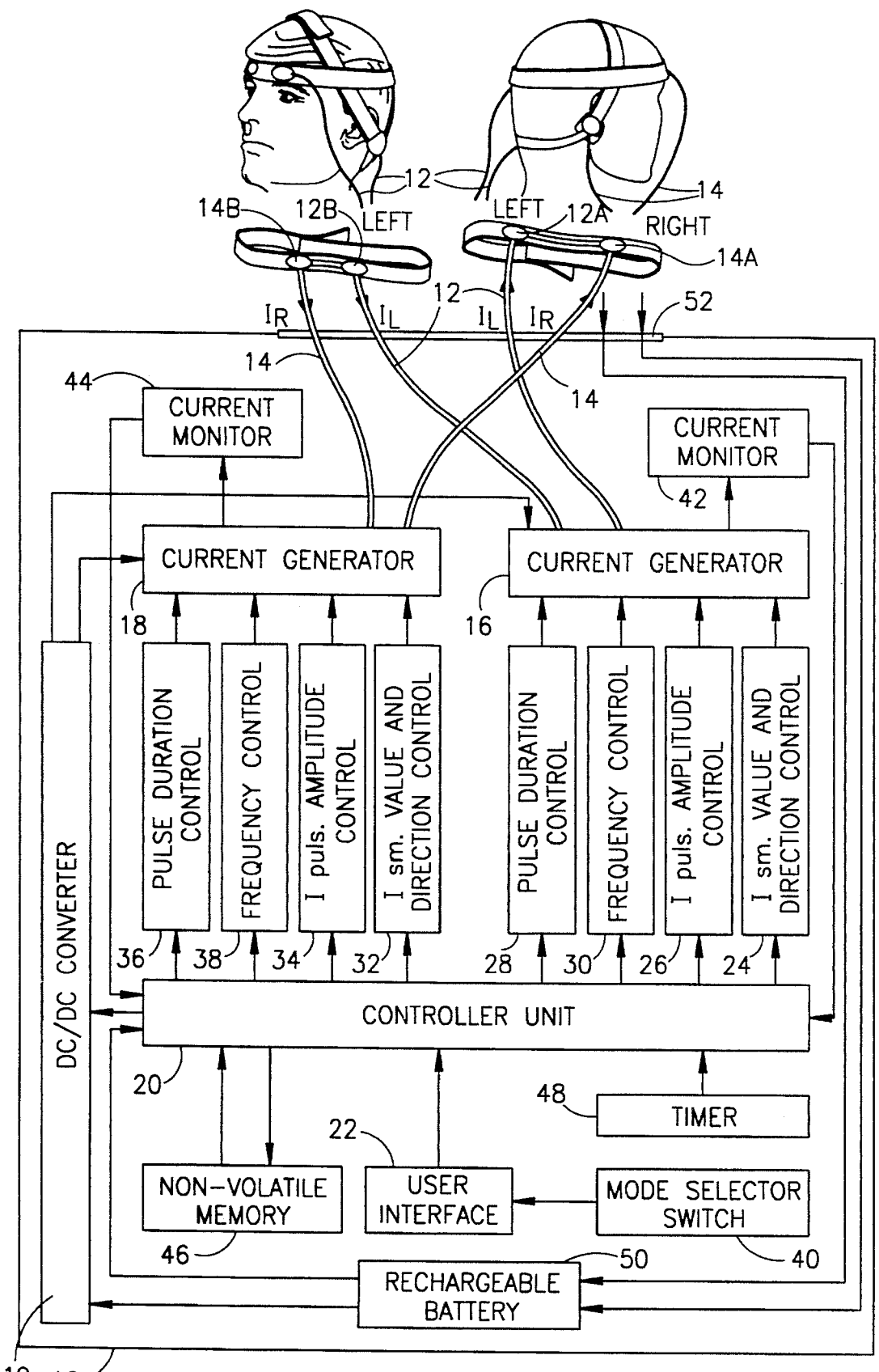
FIG. 2 illustrates a schematic block diagram of a preferred embodiment of a TCES apparatus constructed and operative according to the teachings of the present invention.

Referring now to the drawings, FIG. 2 illustrates a transcranial electrostimulation (TCES) apparatus, generally designated 10, constructed and operative according to the teachings of the present invention, for administering transcranial electrostimulatory treatment to a patient.

TCES apparatus 10 includes a number of electrode pairs for detachable attachment to the scalp of a patient. For the sake of the present example, TCES apparatus 10 is depicted as having two electrode pairs 12 and 14. However, it should be understood that TCES apparatus 10 can include three or more electrode pairs depending on the treatment to be administered to the patient. Electrode pair 12 includes an electrode 12a for detachable attachment to the left mastoid area of the patients' scalp and an electrode 12b for detachable attachment to the left side of the patient's forehead. In a similar fashion, electrode pair 14 includes an electrode 14a for detachable attachment to the right mastoid area of the patient's scalp and an electrode 12b for detachable attachment to the right side of the patient's forehead. Typically, electrodes 12b and 14b are combined as a single electrode.

It is a particular feature of the present invention that TCES apparatus 10 includes an equivalent number of current generators as electrode pairs such that each electrode pair 12 and 14 has an electrode pair dedicated current generator. Hence, in this case, TCES apparatus 10 includes a current generator 16 for driving electrode pair 12 and a current generator 18 for driving electrode pair 14. Current generators 16 and 18 are fed by a DC/DC voltage converter 19 under the control of a microprocessor based controller unit 20. This enables controller unit 20 to interrupt the feeding voltage from DC/DC voltage converter 19 in the case of an electrical hazard to a patient.

Figure 3A:
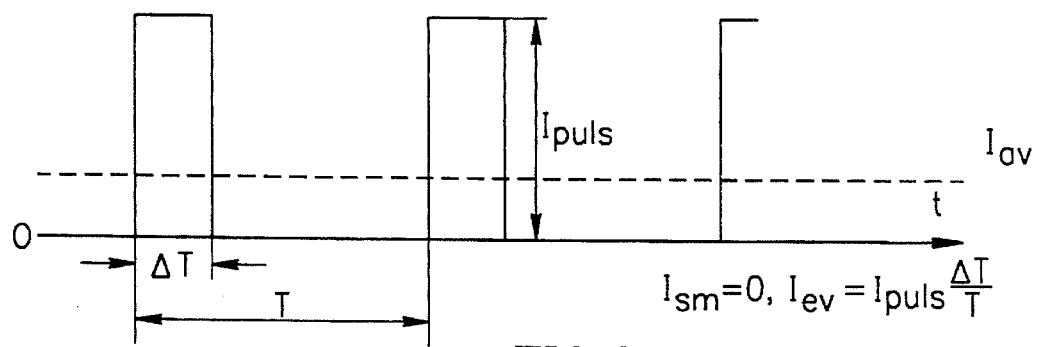
FIG. 3 illustrates different types of electrical signals administered by the TCES apparatus of the present invention.
Figure 3B:
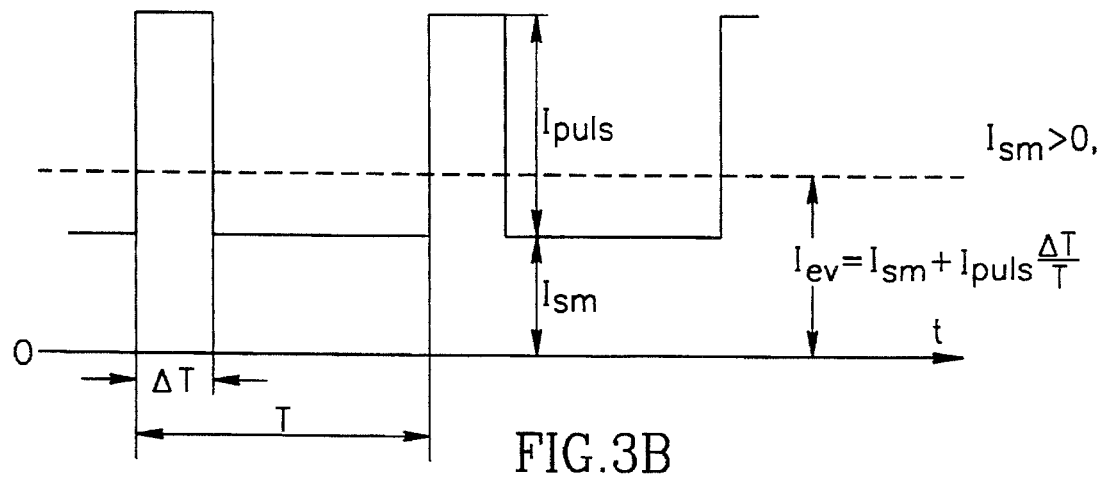
Figure 3C:
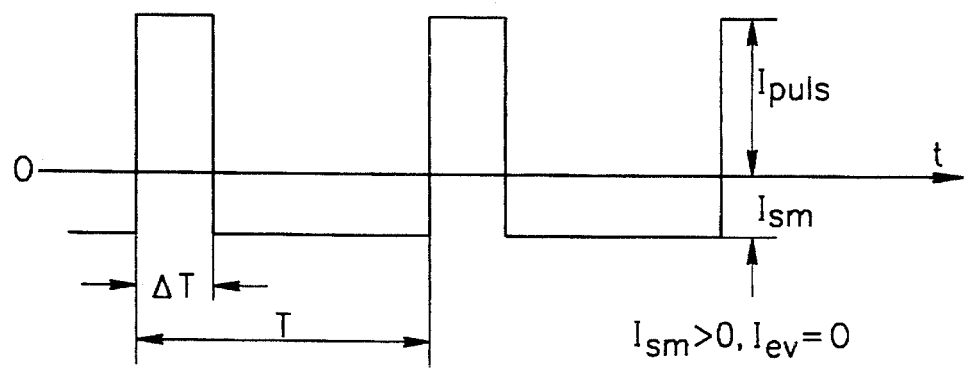

With reference now to FIG. 3, the electrical currents denoted $I_{tot}$ provided by current generators 16 and 18 to induce analgesia are the summation of the following two electrical currents: a smooth electrical current denoted $I_{sm}$ and substantially square shaped electrical pulses denoted $I_{puls}$ such that $I_{tot}=I_{sm}+I_{puls}$. Smooth electrical current $I_{sm}$ can be a zero current (FIG. 3a), a positive current (FIG. 3b) or a negative current (FIG. 3c) while pulse electrical current $I_{puls}$ is a positive current according to the convention that a positive current flows from electrodes 12b and 14b to electrodes 12a and 14a, respectively, and a negative current flows from electrodes 12a and 14a to electrodes 12b and 14b, respectively. The passage of a negative current is to enable the generation of a zero net charge electrical current in the tissue.

Controller unit 20 includes a user interface 22 which enables regulation over the following parameters: the current value of the smooth current, the current amplitude of the pulses relative to the smooth current, the duration of the pulses, and the frequency of the pulses. Thus, each current generator of TCES apparatus 10, in this case, current generators 16 and 18 can administer an independently controllable electrical current to a patient. The average current amplitude $I_{tot}$ is typically in the range of 25 μA - 4 mA. The duration of pulses is typically in the range of 3 msec–4 msec. The frequency of pulses is typically in the range of 75 Hz–85 Hz.

Hence, user interface 22 includes four controls for regulating the electrical current administered by electrode pair 12. First, a smooth current amplitude control 24 for regulating the amplitude of the smooth current. Second, a pulse current amplitude control 26 for regulating the current amplitude of the pulses. Third, a pulse duration control 28 for regulating the duration of the pulses. And fourth, a pulse frequency control 30 for regulating the frequency of the pulses. In a similar fashion, user interface 22 includes a smooth current amplitude control 32, a pulse current amplitude control 34, a pulse duration control 36, and a pulse frequency control 38 for regulating the electrical current administered by electrode pair 14.

User interface 22 also preferably includes a selector switch 40 for determining the mode of operation of TCES apparatus 10. Selector switch 40 typically enables three basic modes of operation. The first mode of operation requires the setting of controls 22–30 for controlling current generator 16 and controls 32–38 for controlling current generator 18. The second mode of operation is for administering a novel net zero charge electrical current described next with reference to FIG. 3c. The third mode of operation is for administering a time-variant electrical stimulatory current which tends to sweep across the homeostatic endorphinergic mid-brain structure of a patient described thereafter with reference to FIG. 4.

Conventional zero net charge electrical currents are achieved by reversing the polarity of consecutive pulses. However, in contrast to conventional zero net charge electrical currents, the zero net charge electrical current according to the teachings of the present invention is achieved by ensuring that the product of the negative smooth current amplitude and the time duration between consecutive pulses equals the product of the positive pulse current amplitude and the pulse time duration. This mode of operation is achieved by realizing current generators 16 and 18 as bilateral current sources and determining the negative current of the smooth current electrical current by the positive pulse current amplitude, the pulse time frequency and the pulse time duration.

Figure 4A:
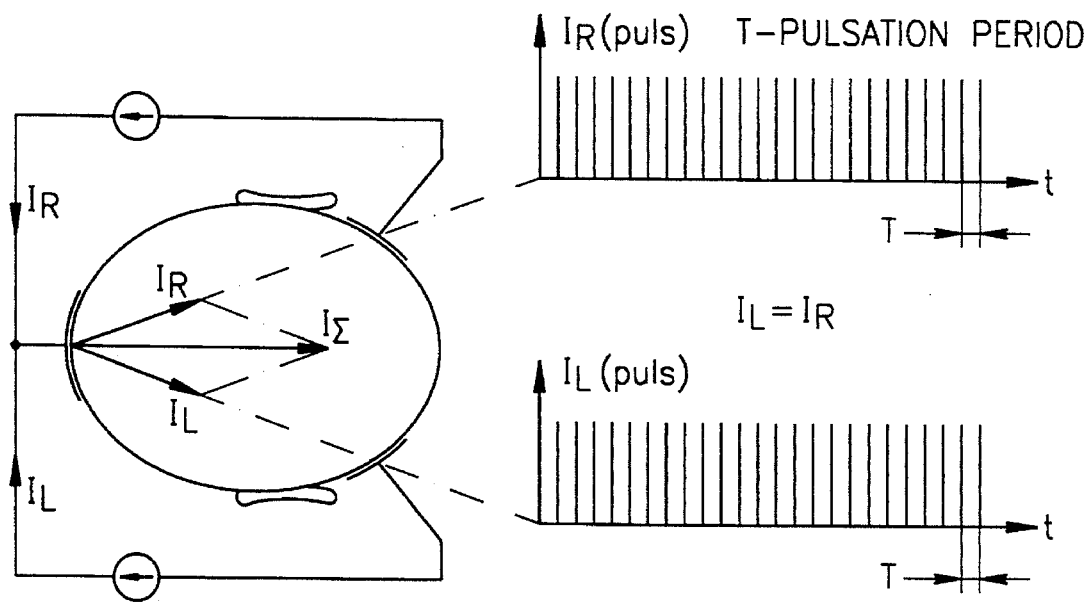
FIG. 4 illustrates a mode of operation of the TCES apparatus of the present invention in which a time-variant electrical stimulatory signal tends to sweep across the homeostatic endorphinergic mid-brain structure of a patient.
Figure 4B:
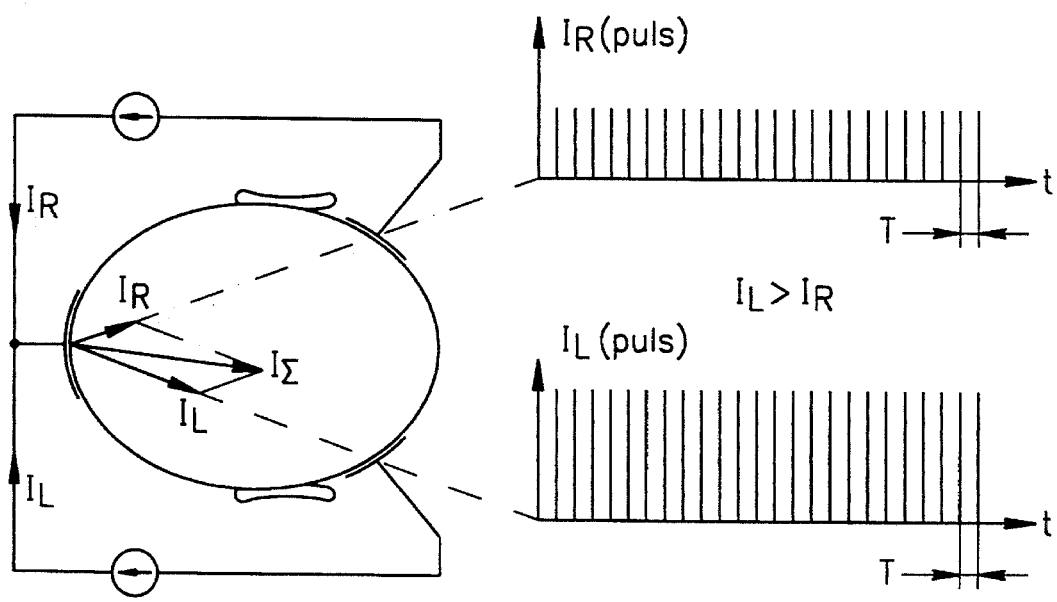
Figure 4C:
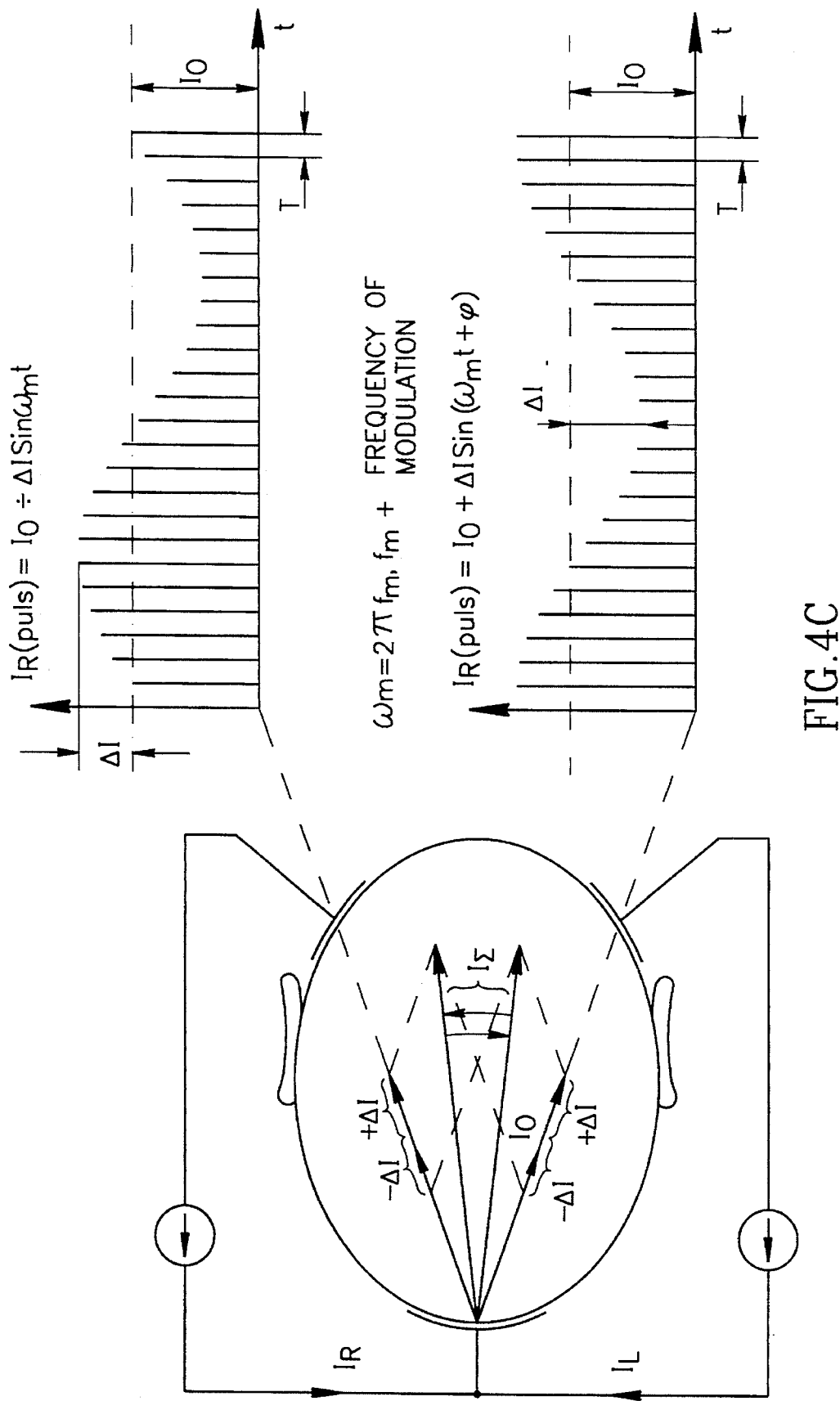

With reference to FIG. 4, it is a further feature of TCES apparatus 10 that current generators 16 and 18 can administer a time-variant electrical stimulatory current which tends to sweep across the homeostatic endorphinergic mid-brain structure of a patient, thereby stimulating more of the mid-brain than the usual time constant electrical currents which traverse the mid-brain along relatively narrow transcranial paths. In particular as shown in FIG. 4c, current generators 16 and 18 typically provide out-of-phase or quadrature modulated currents of equal amplitude such that their combined equivalent acts in effect as a sweeping current denoted $I_\Sigma$.

TCES apparatus 10 further includes current monitors 42 and 44 for measuring the actual current $I_{tot}$ of the electrical currents administered to the patient via electrode pairs 12 and 14, respectively. Thus, current monitor 42 provides feedback to controller unit 20 to enable real time measuring of the electrical current provided by current generator 16 and to actuate alarms if necessary. In a similar fashion, current monitor 44 provides feedback to controller unit 20 to enable real time measuring of the electrical current provided by currents generator 18 and to actuate alarms if necessary. TCES apparatus 10 preferably includes a non-volatile memory 46 for storage of pre-determined treatment regimes and data logging, a timer 48 for determining the duration of a treatment regime, and a number of bio-feedback sensors for facilitating determination of the efficiency of a treatment regime. Typical bio-feedback sensors include a respiration rate sensor, a blood pressure sensor, a heart rate sensor, a skin resistance sensor, body temperature, and the like.

It is a particular feature of TCES apparatus 10 that TCES apparatus 10 includes a novel electrical arrangement so as to prevent electrical shock hazards when a patient is being treated. The novel electrical arrangement includes a rechargeable battery 50 for providing the energy for the electrical pulses to be administered to the patient and a port 52 which is used for both recharging rechargeable battery 50 from an external power supply and for driving electrode pairs 12 and 14. In other words, port 52 can receive either a connector for connecting rechargeable battery 50 to an external power supply or a connector for connecting electrode pairs 12 and 14 to current generators 16 and 18, respectively. In the present instance, port 52 includes 5 pins of which two pins are used for connecting rechargeable battery 50 to an external power supply and three pins are used for connecting electrode pairs 12 and 14 to current generators 16 and 18, respectively. It can be readily appreciated that port 52 can include more pins, for example, for communication purposes.

It should be noted that the above described novel electrical arrangement can be equally implemented for a wide range of electrical devices in which a user faces potential electrical shock hazards. Such devices include, but are not limited to, walkman devices, EEG monitors, ECG monitors, and the like. In each case, the device includes processing means specific to the device and a port including at least three pins of which two are employed for connecting the rechargeable battery to an external power supply and two are employed for connecting the processing means to an output device. It should be noted that in the case that the port includes three pins, one of the pins is used for both connection purposes.

Operation of TCES apparatus 10 is now described. Electrodes pairs 12 and 14 are detachably attached to the scalp of a patient. A physician uses switch selector 40 to select a mode of operation of TCES apparatus 10, for example, the first mode of operation. In this case, the physician sets smooth current amplitude control 24, pulse current amplitude control 26, pulse duration control 28, and pulse frequency control 30 for regulating the electrical current administered by electrode pair 12. In a similar fashion, the physician sets smooth current amplitude control 32, pulse current amplitude control 34, pulse duration control 36 and pulse frequency control 38 for regulating the electrical current administered by electrode pair 14. Alternatively, the physician selects a pre-determined treatment regime from non-volatile memory 46. The physician then sets timer 48. During the treatment, the physician can fine tune the electrical currents administered by current generators 16 and 18 by determining the efficiency of the treatment through feedback from the sensors.

While the invention has been described with respect to a limited number of embodiments, it will be appreciated that many variations, modifications and other applications of the invention may be made.

What is claimed is:

1. Transcranial electrostimulation apparatus for the electrostimulation of a specific portion of a user's brain, comprising:
   (a) at least two current generators for providing electrical currents, said electrical currents including pulses;
   (b) at least two electrode pairs for detachable attachment to the scalp of a patient, each of said at least two electrode pairs being independently driven by one of said current generator; and
   (c) control means for coordinately controlling each of said at least two current generators such that each of said at least two electrode pairs administers a total regulated electrical current so as to target a specific portion of the user's brain.

2. Apparatus as in claim 1 wherein said control means regulates the current amplitude of said pulses.

3. Apparatus as in claim 1 wherein said control means regulates the duration of said pulses.

4. Apparatus as in claim 1 wherein said control means regulates the frequency of said pulses.

5. Apparatus as in claim 1 wherein said pulses are superimposed on a smooth current.

6. Apparatus as in claim 1 wherein said pulses are substantially square shaped.

7. Apparatus as in claim 1 wherein said electrical current is a zero net charge current in which the product of a negative smooth current amplitude by the time duration between consecutive pulses equals the product of a positive pulse current amplitude by the pulse time duration.

8. Apparatus as in claim 1 wherein said electrical current is a time-variant electrical stimulatory current which tends to sweep across the homeostatic endorphinergic mid-brain structure of a patient.

9. Apparatus as in claim 1 wherein each of said at least two current generators includes a bilateral current source.

10. Apparatus as in claim 1 further comprising:
    (d) a rechargeable battery for driving said at least two current generators; and
    (e) a port connected to said battery for receiving either a connector connected to an external power supply so as to charge said rechargeable battery or a connector for connecting said at least two electrode pairs to said at least two current generators.

11. Apparatus as in claim 10 wherein said port includes at least three pins wherein two of said at least three pins are employed for connecting said rechargeable battery to said external power supply.

12. Apparatus as in claim 10 wherein said port includes at least three pins wherein two of said at least three pins are employed for connecting said at least two current generators to said at least two electrode pairs.

* * * * *